(12) United States Patent
King et al.

(10) Patent No.: US 7,742,823 B2
(45) Date of Patent: *Jun. 22, 2010

(54) NEURAL STIMULATION SYSTEM PROVIDING AUTO ADJUSTMENT OF STIMULUS OUTPUT AS A FUNCTION OF SENSED IMPEDANCE

(75) Inventors: John D. H. King, Sherman Oaks, CA (US); James R. Thacker, Eureka, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 11/746,748

(22) Filed: May 10, 2007

(65) Prior Publication Data
US 2007/0208394 A1    Sep. 6, 2007

Related U.S. Application Data

(63) Continuation of application No. 10/364,436, filed on Feb. 11, 2003, now Pat. No. 7,317,948.

(60) Provisional application No. 60/357,008, filed on Feb. 12, 2002.

(51) Int. Cl.
*A61N 1/08* (2006.01)
(52) U.S. Cl. .............. 607/62; 607/8; 607/11; 607/27; 600/547
(58) Field of Classification Search .......... 607/43, 607/46, 62; 600/547, 594
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,570,640 A | 2/1986 | Barsa | |
| 4,735,204 A | 4/1988 | Sussman et al. | |
| 4,911,174 A | 3/1990 | Pederson et al. | |

(Continued)

FOREIGN PATENT DOCUMENTS

WO    WO 97/09863    3/1997

OTHER PUBLICATIONS

Bradley et al, inventor for: U.S. Appl. No. 10/310,202, filed Dec. 3, 2001; entitled "Apparatus and Methods for Determining the Relative Position and Orientation of Neurostimulation Leads".

*Primary Examiner*—Carl H Layno
*Assistant Examiner*—Yun Haeng Lee
(74) *Attorney, Agent, or Firm*—Vista IP Law Group LLP (57) ABSTRACT

A neural stimulation system automatically corrects or adjusts the stimulus magnitude (stimulation energy) in order to maintain a comfortable and effective stimulation therapy. Because the changes in impedance associated with the electrode-tissue interface can indicate obstruction of current flow and positional lead displacement, lead impedance can indicate the quantity of electrical stimulation energy that should be delivered to the target neural tissue to provide corrective adjustment. Hence, a change in impedance or morphology of an impedance curve may be used in a feedback loop to indicate that the stimulation energy needs to be adjusted and the system can effectively auto correct the magnitude of stimulation energy to maintain a desired therapeutic effect.

29 Claims, 6 Drawing Sheets

U.S. PATENT DOCUMENTS

| | | |
|---|---|---|
| 5,184,624 A | 2/1993 | Brown et al. |
| 5,201,865 A | 4/1993 | Kuehn |
| 5,333,618 A | 8/1994 | Lekhtman et al. |
| 5,702,429 A | 12/1997 | King |
| 5,735,887 A | 4/1998 | Barreras, Sr. et al. |
| 5,758,651 A | 6/1998 | Nygard et al. |
| 5,814,092 A | 9/1998 | King |
| 5,895,416 A | 4/1999 | Barreras, Sr. et al. |
| 5,913,882 A | 6/1999 | King |
| 5,941,906 A | 8/1999 | Barreras, Sr. et al. |
| 6,027,456 A | 2/2000 | Feler et al. |
| 6,052,624 A | 4/2000 | Mann |
| 6,181,969 B1 | 1/2001 | Gord |
| 6,195,585 B1 | 2/2001 | Karunasiri et al. |
| 6,205,360 B1 | 3/2001 | Carter et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,516,227 B1 | 2/2003 | Meadows et al. |
| 6,587,724 B2 | 7/2003 | Mann |
| 6,662,053 B2 | 12/2003 | Borkan |
| 6,735,475 B1 | 5/2004 | Whitehurst et al. |
| 6,751,505 B1 | 6/2004 | Van Hen Honert et al. |
| 6,913,763 B2 | 7/2005 | Lerner |
| 6,993,384 B2 | 1/2006 | Bradley et al. |
| 2002/0022866 A1 | 2/2002 | Borkan |
| 2002/0143369 A1 | 10/2002 | Hill et al. |
| 2003/0139781 A1 | 7/2003 | Bradley et al. |
| 2004/0049235 A1 | 3/2004 | Deno et al. |
| 2004/0078067 A1 | 4/2004 | Thompson et al. |
| 2004/0082978 A1 | 4/2004 | Harrison et al. |
| 2004/0116978 A1 | 6/2004 | Bradley |
| 2004/0172083 A1 | 9/2004 | Penner |

NEURAL STIMULATION SYSTEM PROVIDING AUTO ADJUSTMENT OF STIMULUS OUTPUT AS A FUNCTION OF SENSED IMPEDANCE

The present application claims the benefit of U.S. Provisional Patent Application Ser. No. 60/357,008, filed 12 Feb. 2002, which application is herein incorporated by reference. The present application is a continuation of U.S. Ser. No. 10/364,436, filed Feb. 11, 2003, now U.S. Pat. No. 7,317,948.

BACKGROUND OF THE INVENTION

The present invention relates to neural stimulation systems and, more particularly, to an output control system used with such neural systems that automatically maintains the output of the stimulation system at a comfortable and efficacious level.

The present invention may be used in various stimulation therapies in which a neurostimulator is used to stimulate neural tissue. One example where the present invention may be employed is with stimulation of peripheral nerves, e.g., the nerves in the arms, legs, fingers, which nerves are distant from the spinal cord. The present invention may also be used in stimulation of spinal cord nerves.

Spinal cord stimulation (SCS) systems, treat chronic pain by providing electrical stimulation pulses through the electrodes of an electrode array placed epidurally near a patient's spine. SCS is a well-accepted clinical method for reducing pain in certain populations of patients. SCS systems typically include an Implantable Pulse Generator (IPG) coupled to an array of electrodes at or near the distal end of an electrode lead. An electrode lead extension may also be used, if needed. The IPG generates electrical pulses that are delivered to neural tissue, e.g., the dorsal column fibers within the spinal cord, through the electrodes of the electrode array. In an SCS system, for example, the electrodes are implanted proximal to the dura mater of the spinal cord. Individual electrode contacts (the "electrodes") may be arranged in a desired pattern and spacing in order to create an electrode array. Individual wires, or electrode leads, connect with each electrode in the array. The electrode leads exit the spinal cord and attach to the IPG, either directly, or through one or more electrode lead extensions. The electrode lead extension, in turn, when used, is typically tunneled around the torso of the patient to a subcutaneous pocket where the IPG is implanted.

The electrical pulses generated by the SCS stimulation system, or other neural system, are also referred to as "stimulation pulses". In an SCS system, the stimulation pulses typically have the effect of producing a tingling sensation, also known as a paresthesia. The paresthesia helps block the chronic pain felt by the patient. The amplitude, or magnitude, of the stimulation pulses affects the intensity of the paresthesia felt by the patient. In general, it is desirable to have the amplitude of stimulation comfortably set to a level which produces paresthesia to block pain but not above a level that may actually result in pain apart from the native pain. Moreover, the stimulus amplitude should be set to a stimulus level lower than that which can recruit reflex motor nerves that can cause involuntary muscle contractions.

SCS and other stimulation systems are known in the art. For example, an implantable electronic stimulator is disclosed in U.S. Pat. No. 3,646,940 that provides timed sequenced electrical impulses to a plurality of electrodes. As another example, U.S. Pat. No. 3,724,467, teaches an electrode implant for neuro-stimulation of the spinal cord. A relatively thin and flexible strip of biocompatible material is provided as a carrier on which a plurality of electrodes are formed. The electrodes are connected by a conductor, e.g., a lead body, to an RF receiver, which is also implanted, and which is controlled by an external controller.

Representative techniques known in the art for providing for the automatic adjustment of stimulation parameters of an implantable stimulator are disclosed, e.g., in U.S. Pat. Nos. 5,895,416; 5,735,887; 5,333,618; and 4,735,204.

Patients having an SCS system have heretofore had to manually adjust the amplitude of the stimulation pulses produced by their SCS system in order to maintain the paresthesia at a comfortable level. This is necessary for a number of reasons. For example, postural changes, lead array movement (acute and/or chronic), and scar tissue maturation, all affect the intensity of the paresthesia felt by the patient. Because of these changes, i.e., because of postural changes, lead array movement, and scar tissue maturation, as well as other changes that may occur in the patient, the paresthesia can be lost, or can be converted to painful over-stimulation, thereby forcing the patient to manually adjust the output. There is a need for a method or system that would eliminate, or at least mitigate, the need to perform such manual adjustments. Such method or system would be of great benefit to the patient.

SUMMARY OF THE INVENTION

The present invention addresses the above and other needs by providing a neural stimulation system and method that automatically corrects or adjusts the stimulus amplitude in order to maintain a comfortable and effective stimulation therapy. Auto correction of the stimulus amplitude is linked to the measurement of lead impedance, i.e., the impedance measured between selected electrodes.

Because the events that lead to the necessity of an output amplitude change are all associated with how much electrical energy is actually delivered to the neural tissue, and because how much energy is delivered to the neural tissue is, in part, a function of the proximity of the electrodes to the neural tissue, which in turn is a function of the impedance between selected electrodes, the present invention uses a measure of the lead impedance as an indicator of the electrode's effectiveness in providing therapeutic stimulation. Thus, as an event occurs, such as a postural change, lead array movement, or scar tissue maturation, that allows more energy to couple from the emitting electrode or electrodes to the neural tissue, the more likely the stimulus will be painful, i.e., the more likely over-stimulation will occur. Conversely, as an event occurs that attenuates the coupled stimulation energy, the more likely the stimulus will not be sufficient to evoke the desired therapeutic effect (under stimulation).

As indicated above, the present invention uses the measured impedance as an indicator of stimulation energy delivered from the electrode or electrodes to the target neural tissue. The measurement of impedance changes between the stimulation electrodes or neighboring electrodes provides a relative quantitative measure of the electrode array's theoretical effectiveness in providing therapeutic stimulation. The relative change in the measured impedance provides information on the ability of electrical current to flow to the neural tissue. Knowledge of the measured impedance with respect to time allows for the system to effectively auto correct the output amplitude, thereby minimizing the occurrence of over-stimulation or under-stimulation.

One application for the present invention is for a Spinal Cord Stimulation (SCS) system that automatically corrects or adjusts the stimulation amplitude in order to maintain a comfortable and effective paresthesia. As postural change, lead array movement, scar tissue maturation, and the like occur, allowing more energy from the emitting electrode or electrodes of the SCS system to be delivered to the neural tissue, the more likely over-stimulation occurs. Conversely, as events occur that attenuate the coupled energy, the more likely a desired paresthesia does not occur (under stimulation). The relative change in measured impedance is used as a measure of the stimulation energy delivered to the neural tissue. Availability of the measured impedance changes with respect to time allows the system to effectively auto correct the stimulation output amplitude, thereby minimizing the occurrence of over-stimulation (excessive-threshold paresthesia) or under-stimulation (sub-threshold paresthesia).

In accordance with one aspect of the invention, there is provided a neural stimulation system having means for measuring the impedance changes between selected electrodes that occur over time in the epidural space where the electrodes are positioned to be in close proximity to the dura mater of the spinal cord. The system also can provide means for correlating the change in impedance with downward or upward adjustment of stimulation energy. Alternatively, the morphology of the impedance resulting from an event, such as a postural movement may be correlated with the corrective adjustments to stimulation energy. Based on this predetermined correlation, relative impedance changes of significance, i.e., changes indicating that over-stimulation or under-stimulation is likely to occur, are used as triggers to automatically make adjustments, or corrections, in the amplitude of the stimulus current to prevent painful over-stimulation or sub-threshold under-stimulation.

By way of example, as tissue healing (scar maturation) occurs, the impedance may increase, requiring a higher output stimulus to achieve the same therapeutic result. The time frame is a slowly changing increase in impedance with a corresponding increase in the amplitude (or magnitude) of the stimulus output. Hence, the system of the present invention measures the impedance, e.g., usually a heavily weighted impedance average with respect to time, in order to ascertain changes of significance, e.g., changes of more than about 5-10% in the impedance average compared with the impedance average obtained during a reference time in the past. In response to such a slowly moving sensed changes in impedance, the system automatically adjusts the output current or voltage in order to maintain a desired therapeutic effect, e.g., to minimize sub-threshold stimulation or painful over stimulation.

By way of another example, a rapidly changing impedance variation would likely indicate an acute movement of the electrode array surface contact from the proximity of the dura mater. Such a rapid change could be due to a postural change causing the electrode array to move with respect to its location in the epidural space. In accordance with the present invention, when a significant change in average or other weighted measure of impedance, e.g., 10-15%, occurs over a relatively short period of time, e.g., over 10-20 minutes, then such change triggers a corresponding change in the magnitude of the stimulus output in order to maintain a desired therapeutic effect, e.g., to minimize sub-threshold stimulation or painful over stimulation.

In another aspect of the invention an implantable neural stimulator is provided, for autocorrection of stimulation. The stimulator comprises: means for measuring impedance indicative of the coupling efficiency of an electrical stimulation current applied to neural tissue; and means for automatically adjusting the stimulation energy of subsequent stimulation in order to compensate for variations in the measured coupling efficiency.

In yet another aspect of the invention, a method is provided for autocorrection of neuro stimulation, the method comprising: measuring impedance indicative of the coupling efficiency of an electrical stimulation current applied to neural tissue; correlating the decrease or increase of the impedance with an increase or decrease in the stimulation energy delivered to the target neural tissue; and automatically adjusting the subsequent stimulation energy delivered to the neural tissue in order to compensate for variations in the measured coupling efficiency in order to maintain an optimal level of therapy. To measure impedance the following steps may be taken: applying a stimulus having a known amplitude to a first electrode in close proximity to the neural tissue; measuring a voltage developed on the first electrode while the current stimulus is applied thereto; and calculating the impedance as the ratio of the measured voltage to the known current.

It is thus a feature of the present invention to provide a neural stimulation system wherein the output stimulus amplitude is automatically corrected or adjusted in order to compensate for coupling variations in the electrode-to-neural-tissue interface that cause more or less energy to reach the neural tissue from the electrode. In a preferred embodiment, such sensed coupling variations are determined by measuring or monitoring changes in impedance that occur between selected electrodes.

It is a further feature of the invention to provide a method of neural stimulation that includes measuring impedance changes near the location where a stimulus electrode array is located, wherein such impedance changes are indicative of the coupling efficiency of the electrical stimulation current to the neural tissue, and automatically adjusting the magnitude of subsequent stimulating current pulses in order to compensate for variations in the measured coupling efficiency.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
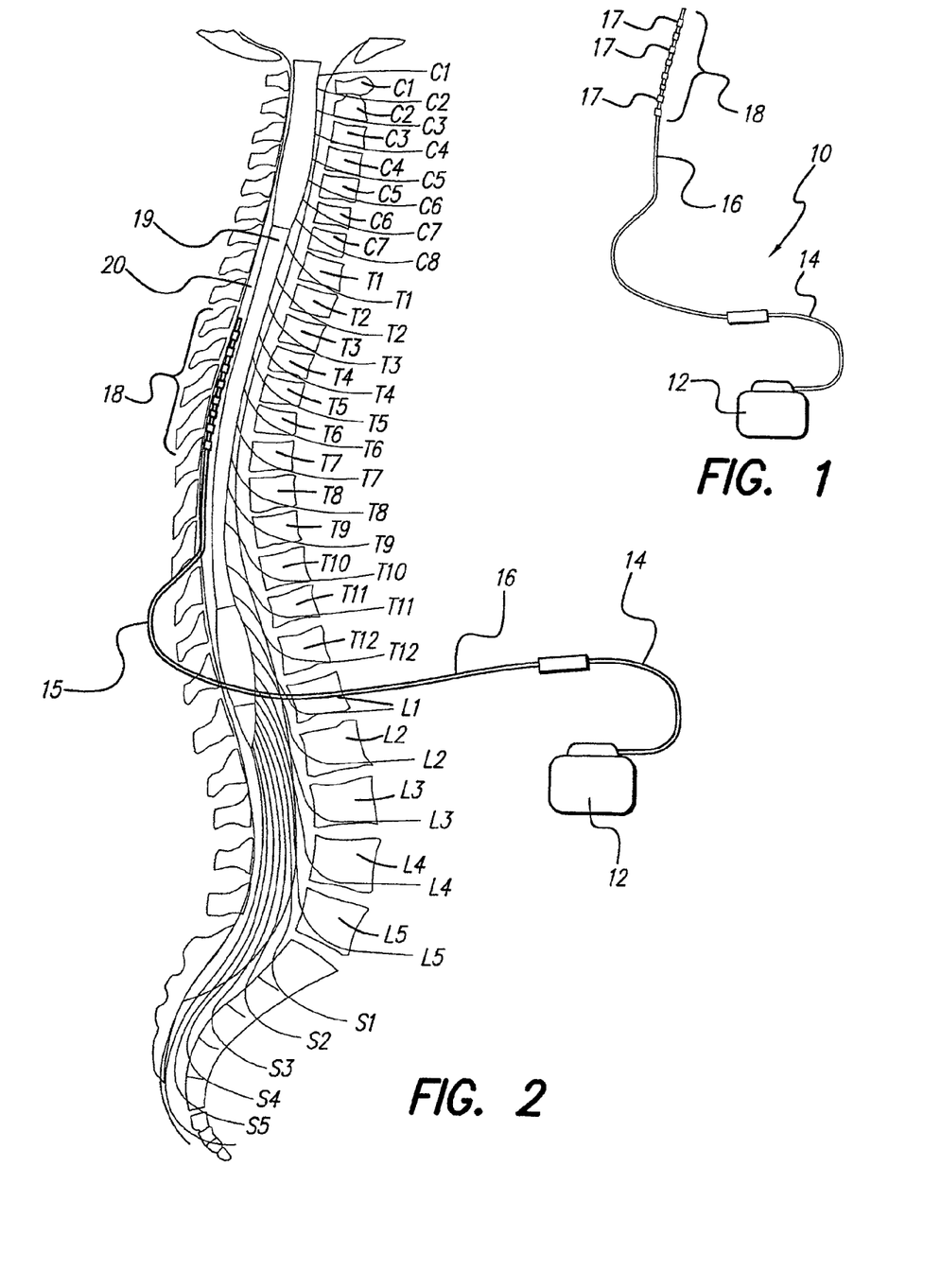
FIG. 1 shows a representative neural stimulation system of the type with which the present invention may be used.
FIG. 2 shows the stimulation system of FIG. 1 being used as a Spinal Cord Stimulation (SCS) system, with the electrode array inserted alongside the spinal cord in the epidural space, in close proximity to the dura mater.

A representative neural stimulation system 10 is shown in FIG. 1. Such a system typically comprises an Implantable Pulse Generator (IPG) 12, a lead extension 14, an electrode lead 16, and an electrode array 18. The electrode array includes a plurality of electrode contacts 17 (also referred to as "electrodes"). The electrodes 17 are arranged, for example, in an in-line array 18 near the distal end of the lead 16. Other electrode array configurations may also be used. The IPG 12 generates stimulation current pulses that are applied to selected ones of the electrodes 17 within the electrode array 18.

A proximal end of the lead extension 14 is removably connected to the IPG 12, and a distal end of the lead extension 14 is removably connected to a proximal end of the electrode lead 16. The electrode array 18, is formed on a distal end of the electrode lead 16. The in-series combination of the lead extension 14 and electrode lead 16, carry the stimulation current from the IPG 12 to electrodes of the electrode array 18. It should be noted that the lead extension 14 need not always be used with the neural stimulation system 10. The lead extension 14 is only needed when the physical distance between the IPG 12 and the electrode array 18 requires its use.

Turning next to FIG. 2, the neural stimulation system 10 is shown being used as a Spinal Cord Stimulator (SCS) system. In such configuration, the lead 16, and more particularly the electrode array 18 is implanted in the epidural space 20 of a patient so as to be in close proximity to the spinal cord 19. Due to the lack of space near the lead exit point 15 where the electrode lead 16 exits the spinal column, the IPG 12 is generally implanted in the abdomen or above the buttocks. The lead extension 14 facilitates locating the IPG 12 away from the lead exit point 15.

A more complete description of an SCS system may be found in U.S. patent application Ser. No. 09/626,010, filed Jul. 26, 2000, now issued as U.S. Pat. No. 6,516,227, which patent is assigned to the same assignee as is the present application, and is incorporated herein by reference in its entirety.

Figure 3A:
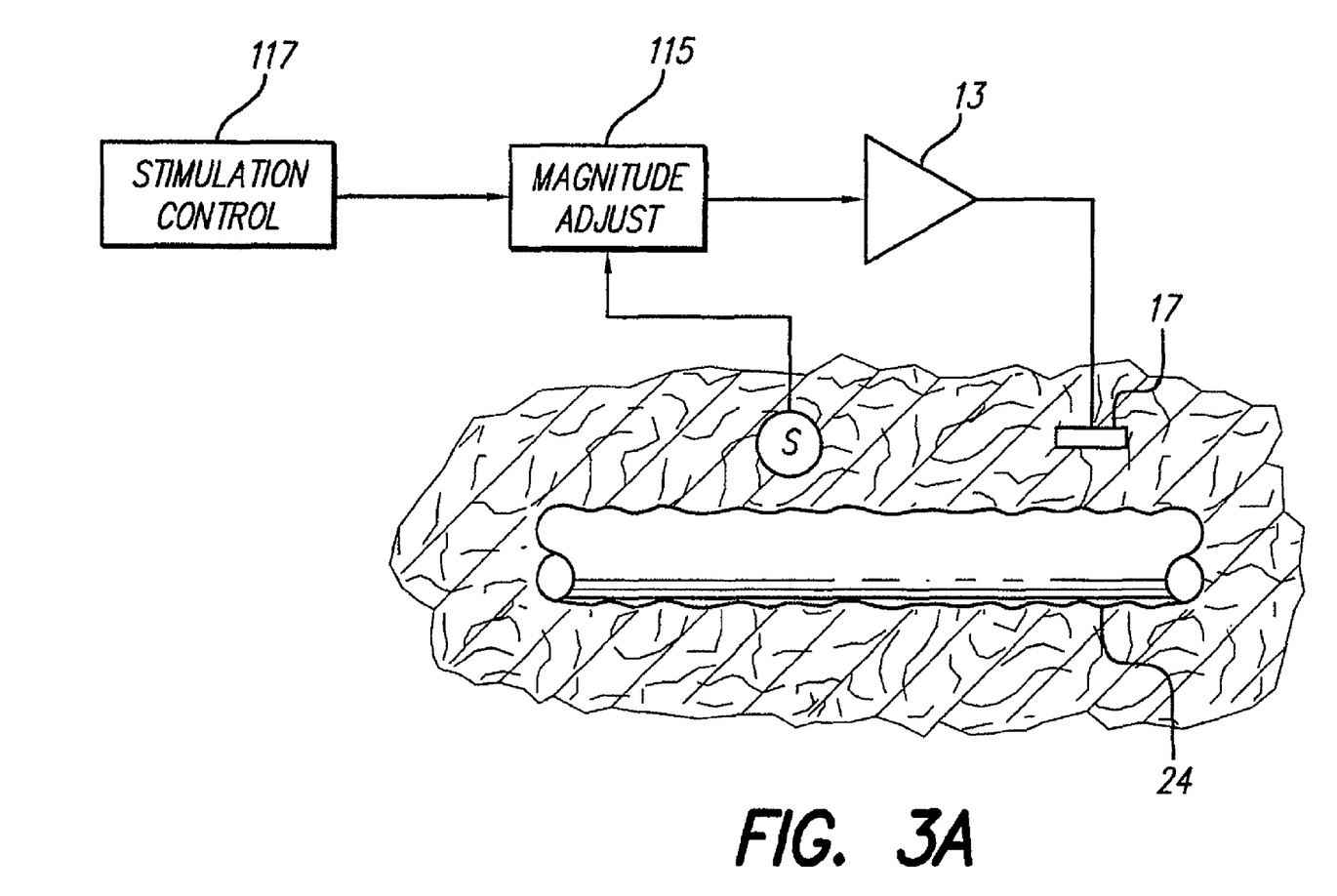
FIG. 3A is a block diagram of a system that automatically adjusts the amplitude of the stimulus current applied to neural tissue in accordance with the present invention.

Next, with respect to FIG. 3A, there is shown a functional block diagram of a system that automatically adjusts the amplitude of the stimulus current applied to neural tissue in accordance with the present invention. As seen in FIG. 3A, an electrode 17 is placed in close proximity to neural tissue 24 that is to be stimulated. The electrode 17 is electrically connected to a current pulse generator 13 which generates a stimulus pulse having a magnitude that is set by magnitude adjust circuitry 115. The magnitude adjust circuitry 115 sets the magnitude of the stimulus pulse as specified by stimulation control circuitry 117. The stimulation control circuitry 117 usually comprises some sort of processor, or state logic, that operates in accordance with a stored program or state diagram. It initially sets the magnitude of the stimulus pulse to a programmed or predetermined value.

As the stimulus pulse is applied to the neural tissue 24, an appropriate impedance sensor S senses the coupling efficiency between the stimulus current and the neural tissue. That is, the impedance sensor S provides a measure of how effective the applied stimulus is at stimulating the neural tissue 24. The sensor S is connected to the magnitude adjust circuitry 115 to provide a feedback signal that indicates whether the magnitude of the stimulus needs to be adjusted up or down. For example, should the impedance measurement with sensor S indicate that very little of the energy is being coupled to the neural tissue 24, then the feedback signal provided through the sensor S automatically causes the magnitude adjust circuitry 115 to increase the magnitude of the stimulus pulse so that the total stimulation energy delivered to the neural tissue 24 remains about the same. Conversely, should the impedance measurement with sensor S indicate that more energy is being coupled to the neural tissue 24, then the feedback signal provided through the sensor S automatically causes the magnitude adjust circuitry 115 to decrease the magnitude of the stimulus pulse so that the total energy delivered to the neural tissue 24 remains about the same. Thus, it is seen that the magnitude adjust circuitry 115 automatically adjusts the magnitude, e.g., the amplitude of the stimulus pulse, so that the stimulation energy delivered to the neural tissue remains more or less the same.

It may be appreciated that while stimulation energy is generally determined by adjusting stimulus amplitude while holding pulsewidth and the pulse frequency (pulses per second) constant, it is also possible to vary the stimulation energy by changing one or more of the stimulus parameters: pulse amplitude, pulsewidth, and frequency.

In accordance with the present invention, coupling efficiency is determined by measuring the impedance between selected electrodes in the vicinity of the electrode-tissue interface. Such impedance measurement can provide a quantitative measure of the stimulating electrode's coupling efficiency between the electrode and neural tissue. For example, as the impedance increases, that means the current flow to the targeted tissue will likely decrease, thereby making the coupling efficiency lower. Conversely, as the impedance decreases, that means the current flow to the targeted tissue will likely increase, thereby making the coupling efficiency higher. Thus, for purposes of the present invention, the sensor S measures impedance associated with the flow of current through the surrounding tissue, including the targeted tissue.

Figure 3B:
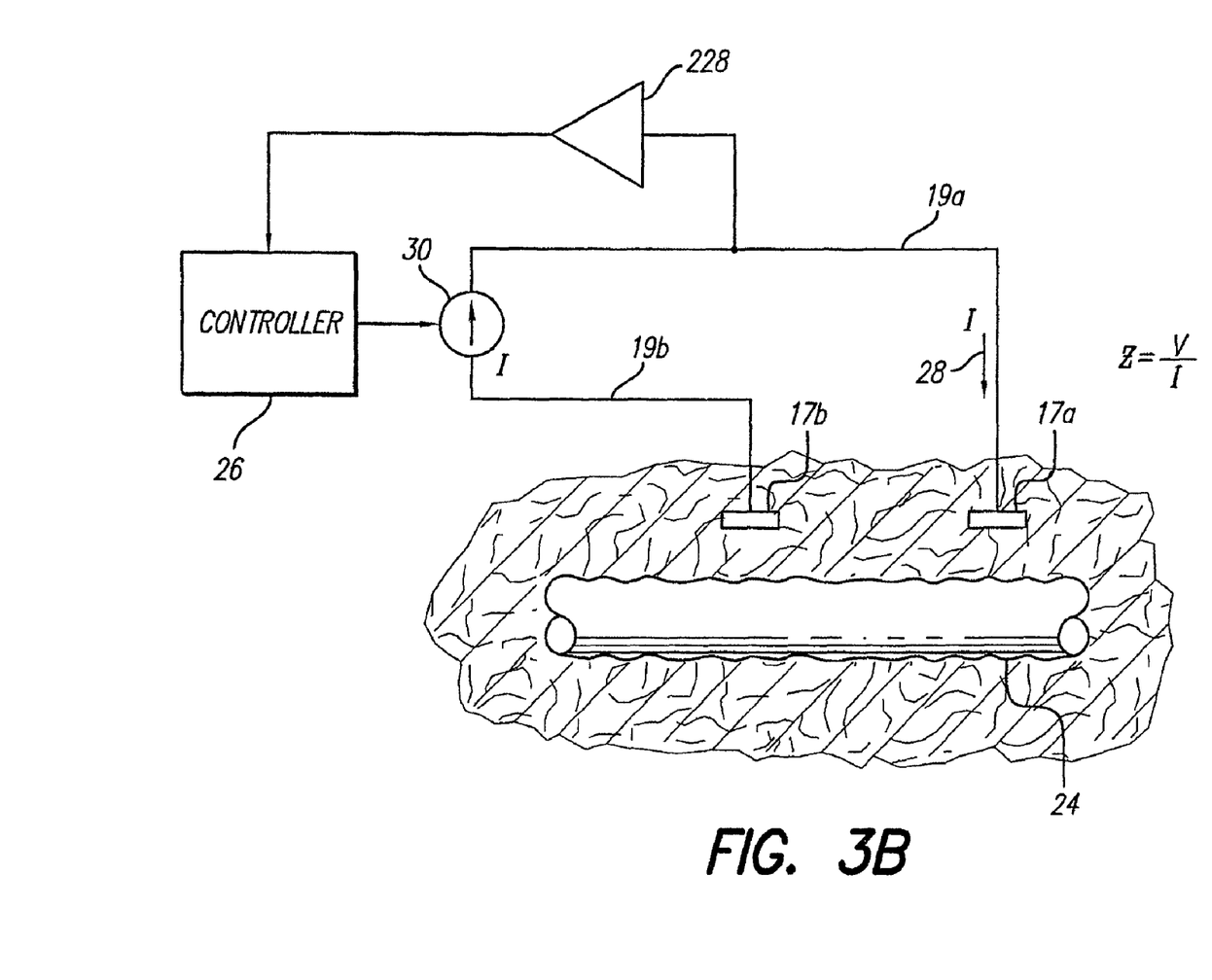
FIG. 3B illustrates one method for sensing or measuring impedance in accordance with the invention.

Next, with respect to FIG. 3B, there is shown one method for measuring impedance. FIG. 3B shows a schematic representation of the electrodes 17a and 17b located at a distal end of a lead. The body of the lead is not shown in FIG. 3B, but it is to be understood that the electrodes 17a and 17b are carried on the lead body, usually near the distal tip, and that the wires 19a and 19b, or equivalent conductors, that attach to the electrodes 17a and 17b, are embedded within the lead body, and exit the lead body near a proximal end, where connection can be made with appropriate electrical circuitry. In a typical neural stimulation system, the lead will have at least one electrode contact, and will usually have a plurality of electrode contacts, e.g., four, eight, sixteen or more electrode contacts. The two electrode contacts 17a and 17b shown in FIG. 3B are intended to be illustrative only, and not limiting. The electrode contacts 17a and 17b are positioned in the epidural space near the dorsal column nerve fibers 24 within or near the spinal cord.

In operation, a stimulation pulse, from a pulse generator 30, is applied to a selected pair of the electrode contacts, e.g., electrode contacts 17a and 17b. As connected in FIG. 3B, the polarity of the pulse generator 30 causes a current, represented by arrow 28, to be emitted from electrode contact 17a and to travel to the neural tissue 24. The current 28 flows through the nerve tissue 24 and surrounding tissue and returns to the pulse generator 30 through electrode contact 17b. The energy contained within the current 28 is coupled to the neural tissue 24 as a function of the coupling efficiency between electrode contacts 17a, 17b and the neural tissue 24. This coupling efficiency may vary, for many reasons, such as postural changes, relative movement between the electrodes 17a and 17b and tissue 24, or scar tissue maturation, to name just a few.

The electrodes 17a and 17b typically fit snugly within the epidural space next to the spinal column. Because the tissue is conductive, there is an impedance, Z, associated therewith that reflects how easily the current flows therethrough. Such impedance provides a good measure of the coupling efficiency between the electrodes and the neural tissue, and thus also provides a relative quantitative measure of the electrode array's theoretical effectiveness in providing therapeutic stimulation.

The impedance may be sensed in various ways. One way is to measure the amount of current that flows through, e.g., conductor 19a or conductor 19b, in response to a known potential or voltage that is placed across the conductors 19a and 19b, and then calculating the impedance Z as the ratio of known voltage to measured current. Another way, depicted in FIG. 3B, is to apply a known current, e.g., from a current source 30, to electrode 17a through conductor 19a, with a return path through electrode 17b and conductor 19b, and then measuring the voltage V, using measurement or buffer amplifier 228, that is developed on conductor 19a as a result of such current flow. The impedance Z may then be calculated by controller 26 as the ratio of measured voltage V to known current I. This impedance may then be stored in memory for later reference, so that the next time an impedance measurement is made, a determination can be made as to whether the impedance has changed, and if so, how much, and what the rate of change is.

It is to be emphasized that the technique shown in FIG. 3B for sensing or measuring impedance is only representative of various ways that may be used. Advantageously, the technique requires no separate sensor, per se, but uses the stimulation electrodes already carried on the lead body. However, if needed, separate electrodes may be carried on the lead body, or carried on another lead body, so that impedance measurements can be made completely independent of the stimulation lead.

Figure 4:
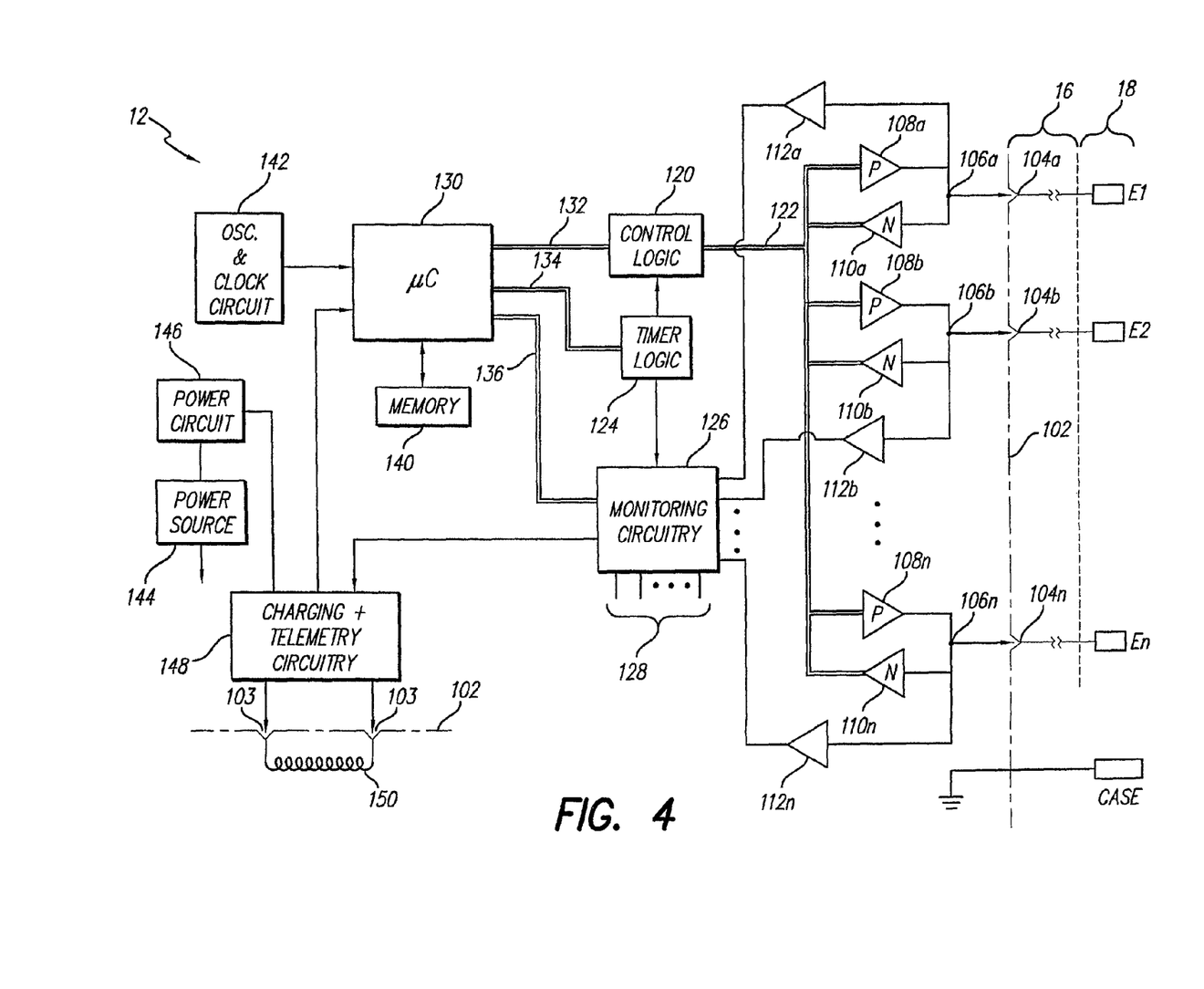
FIG. 4 is a block diagram of a representative Implantable Pulse Generator (IPG) that may be used to practice the present invention.

Turning next to FIG. 4, there is shown a functional block diagram of a representative Implantable Pulse Generator (IPG) 12 (or, with respect to FIG. 3, pulse generator 30) that may be used to practice the present invention. As seen in FIG. 4, the IPG 12 is connected to a multiplicity of electrode contacts E1, E2, . . . En, where n represents an integer of at least 2. The dotted-dashed line 102 in FIG. 4 represents the boundary between the outside of the IPG case, which is exposed to body tissues and fluids when the IPG is implanted, and the inside of the IPG case. The case forms an hermetically sealed compartment wherein the electronic and other components are protected from the body tissues and fluids. Feed-through terminals 104a, 104b, . . . 104n are thus used to provide an electrical path through the IPG case wall 102. The feed-through terminals 104a, 104b, . . . are electrically connected to the electrodes E1, E2, . . . En through wires within the lead 16.

Thus, it is seen that each electrode contact E1, E2, . . . En is connected through a respective feed-through terminal 104a, 104b, . . . 104n to a respective circuit node 106a, 106b, . . . 106n within the hermetically sealed IPG case. This node, in turn is connected to a P-DAC circuit 108a and an N-DAC circuit 110a. Each of the other circuit nodes 106b, . . . 106n within the IPG similarly have a respective P-DAC circuit and N-DAC circuit connected thereto. The P-DAC circuits are used as a programmable current source to generate a precise current value that is emitted from the node to which the P-DAC circuit is connected. Similarly, the N-DAC circuits are used as a programmable current sink that receives a precise current through the node to which the N-DAC circuit is attached. Thus, in operation, one or more P-DAC circuits are programmed to emit a desired current value at the same time that one or more N-DAC circuits are programmed to receive the same desired current value.

A case electrode, CASE, may also be provided that effectively provides a common or return electrode that may be used with some stimulation and sensing configurations, as required.

In operation, in order to generate a stimulus current pulse that is applied between electrodes E1 and E2, for example, the P-DAC circuit 108a, as controlled by control logic 120 over data bus 122, causes a stimulation current having a specified amplitude to be emitted from the node 106a, and hence to be emitted from the electrode contact E1. At the same time, the N-DAC circuit 100b, similarly controlled by control logic 120, causes a stimulation current of the same magnitude to be received through node 106b, and hence through electrode contact E2. Although not shown in FIG. 4, coupling capacitors connect the respective nodes 106 and feed-through terminals 104. With the circuitry described above, a precisely controlled current is generated that flows from electrode contact E1 to electrode contact E2 through whatever body and nerve tissue resides between electrodes E1 and E2. The duration of the current flow, i.e., the width of the current pulse that is generated, is controlled by timer logic circuitry 124. The operation of this output circuitry, including alternative embodiments of suitable output circuitry for performing the same function of generating current stimulus pulses of a prescribed amplitude and width, is described more fully in the above-referenced U.S. patent application Ser. No. 09/626,010, now issued as U.S. Pat. No. 6,516,227.

Voltage sense amplifiers 112a, 112b, . . . 112n are also connected to the respective nodes 106a, 106b, . . . 106n. These sense amplifiers are used to measure the voltage appearing at selected nodes when a known current is flowing through the node. Such voltage measurements, in combination with the known current, allow the impedance to be readily calculated by the monitoring circuitry 126 or processing circuitry 130. Typically, as described more fully below in conjunction with FIG. 5, the impedance measurement is made on a sampled basis during a portion of the time while the stimulus pulse is being applied to the tissue, or immediately subsequent to stimulation. The impedance measurement provides a measure of the coupling efficiency between the electrodes selected to perform the stimulation. The monitoring circuitry 126 also monitors other signals 128 from various locations or components within the IPG, e.g., battery voltage, charge current, etc.

The control logic 120, the timer logic 124, and the monitoring circuit 126 are controlled or watched by a suitable micro-controller (μC) circuit 130. The μC circuit 130 is coupled to the control logic 120, the timer logic 124, and the monitoring circuitry 126 over data buses 132, 134 and 136, respectively.

Suitable memory circuitry 140 is likewise coupled to the μC 130, as is an oscillator and clock circuit 142. The μC 130, in combination with the memory circuit 140 and oscillator and clock circuit 142, thus comprise a microprocessor system that carries out a program function in accordance with a suitable program stored in the memory 140. Alternatively, for some applications, the function provided by the microprocessor system may be carried out by a suitable state machine.

Power for the IPG is provided by a suitable power source 144, such as a rechargeable battery or primary battery. A power circuit 146 can be used to control the charging or replenishment of the power source, as described more fully in the above-referenced patent application Ser. No. 09/626,010, now issued as U.S. Pat. No. 6,516,227.

The power circuit 146, the μC 130 and the monitoring circuitry 126 are also coupled to charging and telemetry circuitry 148. An antenna coil 150 is likewise coupled to the telemetry circuitry 148. It is through the antenna coil 150 that charging, forward telemetry and back telemetry signals may be received and sent to an external device, such as an external programmer or charging circuit, as described more fully in the above-referenced U.S. Pat. No. 6,516,227. In practice, separate coils may be used for charging, forward telemetry and back telemetry functions, as described more fully in the above-referenced '227 patent, but for purposes of the present invention those distinctions are not important.

In FIG. 4, the antenna coil(s) 150 is shown as being outside the hermetically sealed case of the IPG. In such configuration, feed-through terminals 103 are used to allow the coil(s) to be electrically connected to the charging and telemetry circuitry 148, which are inside the hermetically sealed case. Alternatively, if the case is made from a non-ferromagnetic material, such as titanium, or ceramic, the coil(s) 150 may be located inside of the hermetically sealed case.

It is to be emphasized that the schematic illustration shown in FIG. 4 is intended to be functional, and not limiting. Those of skill in the art will be able to fashion appropriate circuitry, whether embodied in digital circuits, analog circuits, software and/or firmware, or combinations thereof, in order to accomplish the desired functions.

Figure 5:
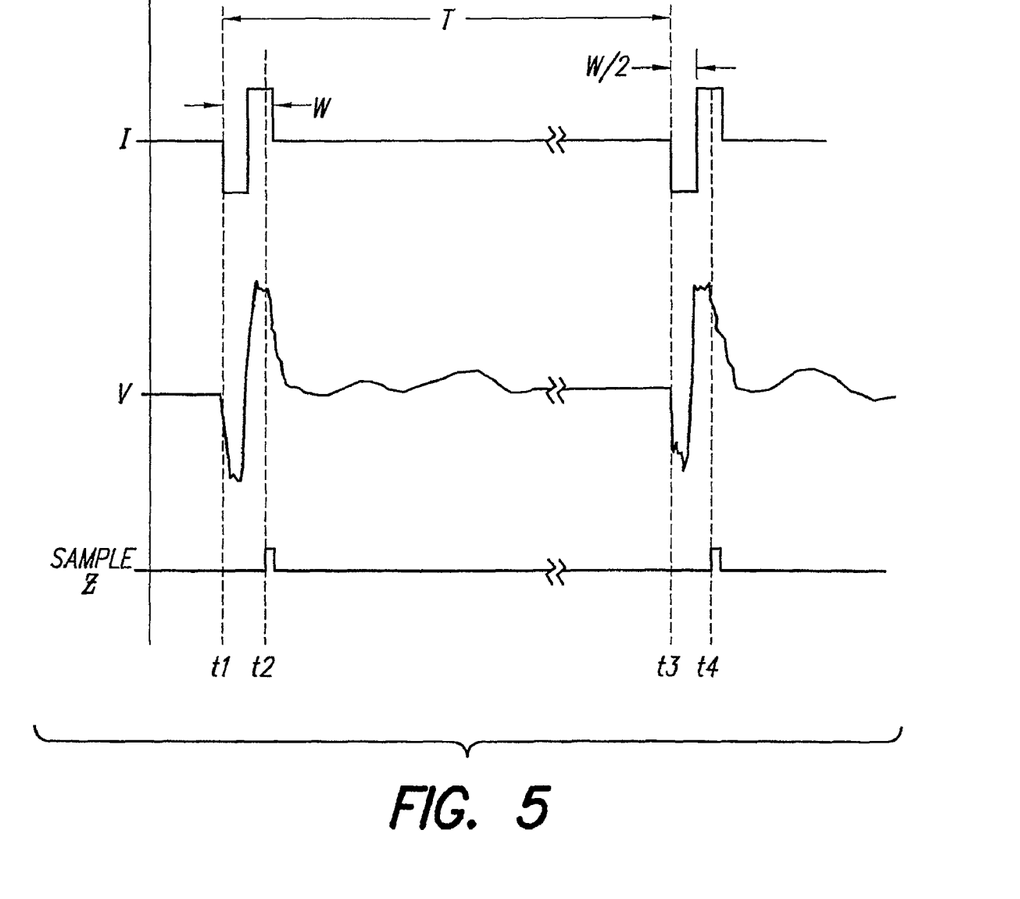
FIG. 5 is a timing waveform diagram that depicts one method for measuring impedance.

FIG. 5 is a timing waveform diagram that depicts one way in which the impedance measurement is made on a sampled basis. As seen in FIG. 5, at time t1, a stimulus current waveform "I" is generated. The waveform "I" is typically a biphasic pulse comprising a negative pulse followed by a positive pulse. The biphasic pulse has a width W. If the stimulus pulse is applied on a recurring basis, e.g., at a set frequency, then there is also a period T between pulses, where the frequency is equal to 1/T. Usually, the biphasic pulse is symmetrical, and the positive and negative portions of the pulse can have an equal width W/2.

As the biphasic stimulus pulse is applied to the tissue, a voltage V is developed across the electrodes through which the current is flows. A representation of such voltage V is shown in the middle waveform of FIG. 5. At an appropriate sample time during the time when the stimulus current pulse "I" is still being applied, e.g., at time t2 near the end of the positive pulse half of the biphasic pulse, the voltage V is measured. The impedance Z is then calculated as Z=V/I.

The impedance measurement will typically be processed in an appropriate manner, e.g., averaged, so that a reliable determination of impedance can be made. Other signal processing techniques such as statistical signal processing techniques may be used that weigh measurements near the average higher than measurements that are far away from the average, as are known in the art. Impedance measurements may also be determined as a bipolar electrode configuration measurement or a monopolar measurement. Such measurements, and other aspects of measuring impedance, are described in co-pending patent application, entitled "Methods for Determination of the Relative Position and Orientation of Neurostimulation Leads", Ser. No. 60/338,331, filed 4 Dec. 2001, which application is assigned to the same assignee as is the present application, and which application is incorporated herein by reference.

In accordance with the present invention, and in response to sensing a significant change in the impedance measurement over time, correction circuitry programmed or wired into the μC 130 causes the amplitude of the stimulation current to also change by a compensating amount.

In one embodiment, the μC 130, or equivalent circuitry, is programmed to ascertain whether the change in impedance is a slow change, which can be caused by scar maturation or fatty tissue build-up. Scar tissue can affect the impedance in certain electrode configurations, e.g., a two lead system with an electrode on each, by changing the distance between electrodes which are used to measure impedance and, in some cases, used as stimulation leads. In general, scar tissue has approximately the same impedance as other living tissues such as fascia and muscle. Thus, it is not the impedance of the scar tissue per se that is usually important, but the fact that development of such scar tissue can push and displace electrode positions relative to each other and relative to the position of the target tissue, which thereby alters the coupling efficiency between stimulation energy emitted from the surface of an electrode contact and stimulation energy actually delivered at the site of a neural tissue. Fatty tissue may change the long-term impedance also by displacing the electrodes and also sometimes by displacing surrounding fluids which are usually more conductive.

A rapid impedance change can be caused by a temporary postural change or by an acute lead movement. Slow changes in impedance are compensated for by making corresponding slow changes in the amplitude of the stimulation current. Rapid changes in impedance, once confirmed through appropriate statistical processing, are similarly compensated for by making rapid changes in the stimulation current, but with automatic rechecking to ascertain whether the change in impedance is temporary or permanent.

It is the energy content of the stimulus pulse that is adjusted in accordance with the invention when a change in the coupling efficiency has been detected. The energy content of the stimulus pulse is readily adjusted by adjusting the amplitude of the stimulus pulse. However, the energy content can also be adjusted by changing the width, or duration, of the stimulus pulse waveform, as well as the frequency with which the stimulus pulse is applied. Thus, as used herein, the term "amplitude" or "magnitude", although commonly used to signify a change in value of a pulse, may instead be understood in the present context to broadly mean the energy content of a stimulus pulse or a train of pulses. Thus, as used herein, a change of stimulus "amplitude" or "magnitude" can occur by changing pulse amplitude, pulsewidth, frequency of the pulses, or any combination thereof.

Figure 6:
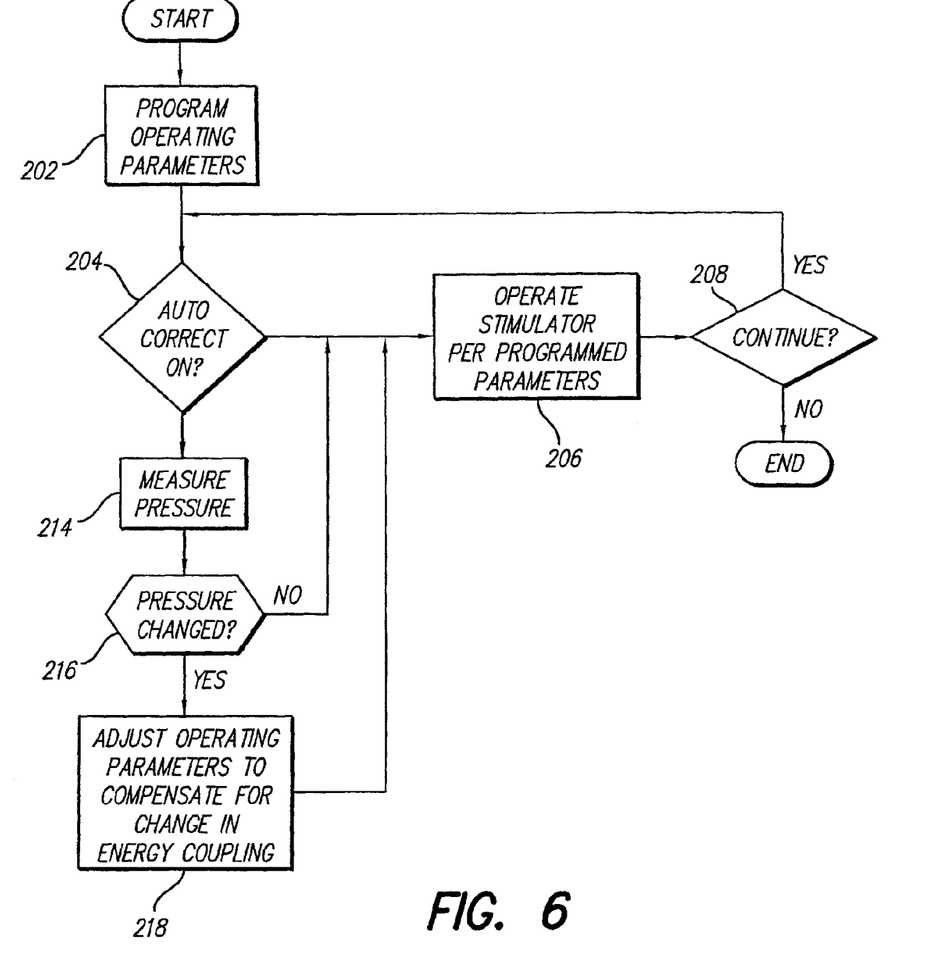
FIG. 6 is a high level flow chart that shows a method of practicing the invention in accordance with one embodiment thereof.

FIG. 6 is a high level flow chart that shows a method of practicing the invention in accordance with one embodiment thereof. A first step involves programming the operating parameters (block 202) into the IPG circuitry. Such operating parameters include not only the operating regime for the neural stimulation system, e.g., stimulation pulse amplitude, pulsewidth, frequency, and electrodes, but also the parameters used by the invention to determine when a sufficient change in the sensed impedance has occurred to trigger the auto correction features of the invention.

As a preliminary matter, because various electrode types may be used in combination with different electrode configurations, it is preferred that each individual patient undergo a lab analysis which correlates the sensed impedance changes with a predicted magnitude adjustment to the stimulation emanating from the selected at least one electrode in the array of electrode E1 . . . En. In a simple case, it is determined whether an increase in impedance (comparing at least two impedance samples) corresponds to an adjustment requiring an increase or decrease in the stimulation energy. To obtain this correlation data, the patient can be instructed to make various positional changes while a test stimulus current, similar to that shown in FIG. 5, is applied through a stimulating electrode and responsive impedance measurements can be recorded as a function of the positional changes. In addition, it may be necessary to vary the stimulus during the assessment test to determine the just noticeable stimulation ("perception threshold") at a particular patient position and the "maximum comfortable" level of stimulation in order to interpolate and correlate the impedance change with the corresponding adjustment to be made to the stimulation energy delivered to the neural tissue. This correlation data can be stored into memory 140 or other long-term memory in the IPG and can be recalled later to analyze the indication of each sensed change in impedance.

A more sophisticated method for correlating an event change with a change in impedance uses impedance morphology or the plotted curve of the impedance as a function of time. An event that causes a short-term impedance change may have a characteristic resulting impedance morphology. For example, impedance changes caused by body movements may have different impedance morphologies. If an impedance morphology can be linked to an associated corrective adjustment, when that same morphology is sensed by the IPG, the proper corrective adjustment may be applied automatically.

A specific method of implementing this link is to generate a correlation table ("look-up" table) which may be developed for different body movements, for example. A short-term postural change ("an event") may occur over an event time, $T_e$. The types of postural events that should be included in the catalog of short term body movements are those movements normally made during the day, e.g., sitting to lying, standing to lying, lying to standing, sitting to standing, twisting the torso to one or the other side, standing to sitting (in a chair) and vice versa, standing to sitting (on a stool) and vice versa, running etc. Each of these events must be characterized in the laboratory for each individual patient to generate a personalized look-up table that correlates the body movements/events with a characteristic impedance waveform morphology, over a time, $T_e$. In addition, for each event characterized, there is linked a corresponding predicted adjustments (up or down) to the stimulation energy, which may be adjusted, through magnitude adjust 115, by varying pulse amplitude, pulsewidth, and pulse frequency.

To obtain usable impedance morphology associated with each body movement, it is necessary that a sufficient number of impedance values are sampled with the event time, $T_e$. The IPG 12 can have automatic capability to capture impedance (V/I) datapoints over a recording or sampling duration, $T_r$, which should be greater than $T_e$ to capture the entire waveform. These data may be uplinked to an external programmer (not shown) having processing capability or, alternatively, a computer which can be used to analyze and set the corrective stimulus adjustments. After the entire look-up table is generated, including corrective stimulus adjustments linked one-to-one to each stored characteristic morphology, the data table can be downloaded to the IPG to be stored in memory. In accordance with the method of the present invention, this look-up table may then be recalled by software in the IPG to make nearly instantaneous corrective adjustments to stimulation energy as a function of an identified short-term, impedance morphology.

Once all the operating parameters have been programmed, a determination is made as to whether the auto correction feature of the invention has been programmed ON (block 204). If not, then the stimulator operates in accordance with its programmed operating regime without invoking the auto correction feature (block 206). Unless such programmed operating regime is turned off (block 208), this process continues.

If auto correction is turned ON (block 204), then an impedance measurement is made (block 214), e.g., by sampling the voltage on the electrode at a time when a known current is flowing to the electrode. Once an impedance measurement has been made, then a determination is made as to whether the impedance has changed (block 216). If not, then the operation of the stimulator continues in accordance with its programmed parameters (block 206), and the process continues.

If a determination is made that the impedance (size and/or morphology) has changed (block 216), then the operating parameters, e.g., stimulation current amplitude, are adjusted to compensate for the change in energy coupling (block 218), and the stimulator is operated in accordance with such newly adjusted parameters (block 206). The selection of the stimulus amplitude (or energy) may be based on predetermined calculations or based on a pre-programmed lookup table as previously described. In this manner, a negative feedback is provided through use of the impedance measurement to maintain the energy coupling and the energy delivered to the neural tissue at substantially a constant or programmed level. The set level for maintaining the energy delivered to the neural tissue may be a pre-programmed single level or it may be a pre-programmed stimulation energy range that provides a response that is above the just noticeable stimulation ("perception threshold") and below the maximum comfortable stimulation. Stimulation energies above the maximum comfortable stimulation level will cause pain.

It is emphasized that while the present invention has been explained specifically in the context of the SCS application, the present invention can be practiced where the nerve stimulated is a peripheral, as well as a spinal cord nerve. All figures except FIG. 2 apply equally to the case of stimulating peripheral nerve. FIG. 1 shows an in-line electrode array 18 whereas, in comparison, with a peripheral nerve application a different lead type and electrode configuration may be used. Peripheral nerve application also differs from SCS application in that the results of stimulation provide different physical results. In SCS, sensory fibers are stimulated. In peripheral nerve application, sensory nerves are stimulated which innervate arms and legs. The method and system of the present invention is not dependent, however, on a specific type of lead or electrode configuration used. Rather, the present invention can be applied equally effectively for the purpose of autocorrecting stimulation energy applied to peripheral nerve stimulation following a detected change in impedance. Thus, it is within the contemplation of the present invention to include within its scope the application where peripheral nerve is stimulated.

As described above, it is thus seen that the present invention provides a neural stimulation system wherein the output stimulus magnitude is automatically corrected or adjusted in order to compensate for coupling efficiency variations in the electrode-to-neural-tissue interface that cause more or less energy to reach the neural tissue from the electrode. Variations in the coupling efficiency are determined, in a preferred embodiment, by sensing changes in electrode impedance in the vicinity of the electrode-tissue interface.

As further described above, it is seen that the invention provides a method of neural stimulation that includes measuring the impedance at or near the electrode-tissue interface, which measurements are indicative of the coupling efficiency of the electrical stimulation current to the neural tissue, and which measurement may be used in a feedback loop to automatically adjust the magnitude of subsequent stimulus pulses in order to compensate for variations in the measured coupling efficiency.

While the invention herein disclosed has been described by means of specific embodiments and applications thereof, numerous modifications and variations could be made thereto by those skilled in the art without departing from the scope of the invention set forth in the claims.

What is claimed is:

1. A method of neural stimulation using a neurostimulator, the method comprising:
    correlating impedance changes with predicted stimulation energy adjustments;
    initially storing the correlated measured impedance changes and predicted stimulation energy adjustments in a look-up table;
    measuring a change in impedance indicative of variations in the coupling efficiency between stimulation energy output from the neurostimulator and neural tissue;
    subsequently analyzing the stored correlated measured impedance changes and predicted stimulation energy adjustments to determine the predicted stimulation energy adjustment correlated to the measured impedance change; and
    automatically adjusting the stimulation energy output from the neurostimulator accordance with the determined stimulation energy adjustment to compensate for the variations in the coupling efficiency by maintaining the stimulation energy delivered to the neural tissue at a set level.

2. The method of claim 1, wherein the stimulation energy output from the neurostimulator is automatically adjusted by varying pulse amplitude, pulsewidth, frequency of pulses or some combination of these three stimulus parameters.

3. The method of claim 1, further comprising cross-referencing the measured impedance change with the correlated impedance changes to determine the adjustment of the stimulation energy output from the neurostimulator.

4. The method of claim 1, wherein the impedance changes are correlated with the predicted stimulation energy adjustments by having a patient implanted with the neurostimulator make positional movements to induce changes in measured impedance and recording impedance measurements as a function of the positional movements.

5. The method of claim 4, wherein the positional movements comprise sitting to lying, standing to lying, sitting to standing, twisting the torso to one or the other side, standing to sitting, and running.

6. The method of claim 4, wherein the impedance changes are correlated with the predicted stimulation energy adjustments further by recording associated changes in sensation reported by the patient.

7. The method of claim 4, wherein the impedance changes are correlated with the predicted stimulation energy adjustments further by varying the stimulation energy output from the neurostimulator at each particular patient position and determining the perception threshold at the particular patient position and the maximum comfort level at the particular patient position.

8. The method of claim 1, wherein the correlated impedance changes are characteristic impedance waveform morphologies, the impedance change measurement comprises measuring a characteristic impedance waveform morphology, and the stimulation energy output from the neurostimulator is automatically adjusted based on the predicted stimulation energy adjustments and the measured characteristic impedance waveform morphology.

9. A method of neural stimulation using a neurostimulator, the method comprising:
    correlating impedance changes with predicted stimulation energy adjustments;
    measuring a change in impedance indicative of variations in the coupling efficiency between stimulation energy output from the neurostimulator and neural tissue, wherein the change in impedance is measured by taking at least two impedance samples over time and comparing the at least two impedance measurements to each other;
    cross-referencing the measured impedance change with the correlated impedance changes to determine the adjustment of the stimulation energy output from the neurostimulator; and
    automatically adjusting the stimulation energy output from the neurostimulator in accordance with the determined adjustment of the stimulation energy output in order to compensate for the variations in the coupling efficiency.

10. The method of claim 9, wherein the stimulation energy output from the neurostimulator is automatically by varying pulse amplitude, pulsewidth, frequency of pulses or some combination of these three stimulus parameters.

11. The method of claim 9, further comprising initially storing the correlated measured impedance changes and predicted stimulation energy adjustments.

12. The method of claim 11, wherein the correlated measured impedance changes and predicted stimulation energy adjustments are stored in a look-up table.

13. The method of claim 9, wherein the impedance changes are correlated with the predicted stimulation energy adjustments by having a patient implanted with the neurostimulator make positional movements to induce changes in measured impedance and recording impedance measurements as a function of the positional movements.

14. The method of claim 13, wherein the positional movements comprise sitting to lying, standing to lying, sitting to standing, twisting the torso to one or the other side, standing to sitting, and running.

15. The method of claim 13, wherein the impedance changes are correlated with the predicted stimulation energy adjustments further by recording associated changes in sensation reported by the patient.

16. The method of claim 13, wherein the impedance changes are correlated with the predicted stimulation energy adjustments further by varying the stimulation energy output from the neurostimulator at each particular patient position and determining the perception threshold at the particular patient position and the maximum comfort level at the particular patient position.

17. The method of claim 9, wherein the correlated impedance changes are characteristic impedance waveform morphologies, the impedance change measurement comprises measuring a characteristic impedance waveform morphology, and the measured impedance waveform morphology is cross-referenced with the correlated characteristic impedance waveform morphologies to determine the adjustment of the stimulation energy output from the neurostimulator.

18. The method of claim 9, wherein the stimulation energy output from the neurostimulator is automatically adjusted to compensate for the variations in the coupling efficiency by maintaining the stimulation energy delivered to the neural tissue at a set level.

19. A method of neural stimulation using a neurostimulator, the method comprising:
    correlating impedance changes with predicted stimulation energy adjustments by having a patient implanted with the neurostimulator make positional movements to induce changes in measured impedance and recording impedance measurements as a function of the positional movements;

measuring a change in impedance indicative of variations in the coupling efficiency between stimulation energy output from the neurostimulator and neural tissue; and automatically adjusting the stimulation energy output from the neurostimulator based on the predicted stimulation energy adjustments and the measured impedance change to compensate for the variations in the coupling efficiency by maintaining the stimulation energy delivered to the neural tissue at a set level.

20. The method of claim 19, wherein the stimulation energy output from the neurostimulator is automatically adjusted by varying pulse amplitude, pulsewidth, frequency of pulses or some combination of these three stimulus parameters.

21. The method of claim 19, further comprising:
initially storing the correlated measured impedance changes and predicted stimulation energy adjustments; and
subsequently analyzing the stored correlated measured impedance changes and predicted stimulation energy adjustments to determine the predicted stimulation energy adjustment correlated to the measured impedance change.

22. The method of claim 19, wherein the positional movements comprise sitting to lying, standing to lying, sitting to standing, twisting the torso to one or the other side, standing to sitting, and running.

23. The method of claim 19, wherein the impedance changes are correlated with the predicted stimulation energy adjustments further by recording associated changes in sensation reported by the patient.

24. The method of claim 19, wherein the impedance changes are correlated with the predicted stimulation energy adjustments further by varying the stimulation energy output from the neurostimulator at each particular patient position and determining the perception threshold at the particular patient position and the maximum comfort level at the particular patient position.

25. The method of claim 19, wherein the correlated impedance changes are characteristic impedance waveform morphologies, the impedance change measurement comprises measuring a characteristic impedance waveform morphology, and the stimulation energy output from the neurostimulator is automatically adjusted based on the predicted stimulation energy adjustments and the measured characteristic impedance waveform morphology.

26. A method of neural stimulation using a neurostimulator, the method comprising:
correlating characteristic impedance waveform morphologies with predicted stimulation energy adjustments;
measuring a characteristic impedance waveform morphology indicative of variations in the coupling efficiency between stimulation energy output from the neurostimulator and neural tissue; and
automatically adjusting the stimulation energy output from the neurostimulator based on the predicted stimulation energy adjustments and the measured characteristic impedance waveform morphology to compensate for the variations in the coupling efficiency by maintaining the stimulation energy delivered to the neural tissue at a set level.

27. The method of claim 26, wherein the stimulation energy output from the neurostimulator is automatically adjusted by varying pulse amplitude, pulsewidth, frequency of pulses or some combination of these three stimulus parameters.

28. The method of claim 26, further comprising:
initially storing the correlated measured characteristic impedance waveform morphologies and predicted stimulation energy adjustments; and
subsequently analyzing the stored correlated measured characteristic impedance waveform morphologies and predicted stimulation energy adjustments to determine the predicted stimulation energy adjustment correlated to the measured characteristic impedance waveform morphology.

29. The method of claim 26, wherein the characteristic impedance waveform morphologies are correlated with the predicted stimulation energy adjustments by having a patient implanted with the neurostimulator make positional movements to induce changes in measured characteristic impedance waveform morphologies and recording characteristic impedance waveform morphology measurements as a function of the positional movements.

* * * * *